United States Patent
Clark

(10) Patent No.: US 9,686,942 B2
(45) Date of Patent: Jun. 27, 2017

(54) WHEAT CULTIVAR BZ9S09-0133W

(71) Applicant: Monsanto Technology LLC, St. Louis, MO (US)

(72) Inventor: Dale R. Clark, Bozeman, MT (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 15/048,771

(22) Filed: Feb. 19, 2016

(65) Prior Publication Data

US 2016/0249580 A1 Sep. 1, 2016

Related U.S. Application Data

(60) Provisional application No. 62/126,113, filed on Feb. 27, 2015.

(51) Int. Cl.
*A01H 5/10* (2006.01)

(52) U.S. Cl.
CPC ...................................... *A01H 5/10* (2013.01)

(58) Field of Classification Search
None
See application file for complete search history.

(56) References Cited

U.S. PATENT DOCUMENTS 5,523,520 A 6/1996 Hunsperger et al.
8,872,007 B2 * 10/2014 Shantz ............... C12N 15/8289
426/549

OTHER PUBLICATIONS

Allard, In: Principles of Plant Breeding, Chapter 6 through Chapter 9, University of California, Davis, California, John Wiley & Sons, New York, pp. 50-98, 1960.
Eshed et al., "Less-than-additive epistatic interactions of quantitative trait loci in tomato," *Genetics*, 143:1807-1817, 1996.
Kraft et al., "Linkage disequilibrium and fingerprinting in sugar beet," *Theor Appl Genet*, 101:323-326, 2000.
Poehlman, J.M. and Sleper, D.A., "Methods in Plant Breeding," In Breeding Field Crops, 4th ed., Iowa State Press, pp. 159-239, 1995.
Fehr, Iowa State University, "Principles of Cultivar Development," vol. 1 Theory and Technique and vol. 2 Crop Species, Soybean, Macmillian Publishing Company, New York, pp. 360-376, 1987.
Vaariety specific information as indicated in transmittal letter of May 6, 2016 Information Disclosure Statement for U.S. Appl. No. 15/048,771.

\* cited by examiner

*Primary Examiner* — Cynthia Collins
(74) *Attorney, Agent, or Firm* — Dentons US LLP

(57) ABSTRACT

The invention relates to the wheat cultivar designated BZ9S09-0133W. Provided by the invention are the seeds, plants and derivatives of the wheat cultivar BZ9S09-0133W. Also provided by the invention are tissue cultures of the wheat cultivar BZ9S09-0133W and the plants regenerated therefrom. Still further provided by the invention are methods for producing wheat plants by crossing the wheat cultivar BZ9S09-0133W with itself or another wheat cultivar and plants produced by such methods.

24 Claims, No Drawings

WHEAT CULTIVAR BZ9S09-0133W

This application claims the benefit of U.S. provisional application No. 62/126,113, filed Feb. 27, 2015, which is herein incorporated by reference in its entirety.

BACKGROUND OF THE INVENTION

Field of the Invention

The present invention relates generally to the field of wheat breeding. In particular, the invention relates to the new and distinctive wheat cultivar BZ9S09-0133W.

Description of Related Art

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to drought and heat, better agronomic quality, resistance to herbicides, and improvements in compositional traits.

Wheat may be classified into six different market classes. Five of these, including common wheat, hard red winter, hard red spring, soft red winter, and white, belong to the species *Triticum aestivum* L., and the sixth, durum, belongs to the species *Triticum turgidum* L. Wheat may be used to produce a variety of products, including, but not limited to, grain, flour, baked goods, cereals, crackers, pasta, beverages, livestock feed, biofuel, straw, construction materials, and starches. The hard wheat classes are milled into flour used for breads, while the soft wheat classes are milled into flour used for pastries and crackers. Wheat starch is used in the food and paper industries as laundry starches, among other products.

SUMMARY OF THE INVENTION

One aspect of the present invention relates to seed of the wheat cultivar BZ9S09-0133W. The invention also relates to plants produced by growing the seed of the wheat cultivar BZ9S09-0133W, as well as the derivatives of such plants. Further provided are plant parts, including cells, plant protoplasts, plant cells of a tissue culture from which wheat plants can be regenerated, plant calli, plant clumps, and plant cells that are intact in plants or parts of plants, such as leaves, stems, roots, root tips, anthers, pistils, seed, grain, pericarp, embryo, pollen, ovules, cotyledon, hypocotyl, spike, floret, awn, lemma, shoot, tissue, petiole, cells, and meristematic cells, and the like.

In a further aspect, the invention provides a composition comprising a seed of wheat cultivar BZ9S09-0133W comprised in plant seed growth media. In certain embodiments, the plant seed growth media is a soil or synthetic cultivation medium. In specific embodiments, the growth medium may be comprised in a container or may, for example, be soil in a field. Plant seed growth media are well known to those of skill in the art and include, but are in no way limited to, soil or synthetic cultivation medium. Advantageously, plant seed growth media can provide adequate physical support for seeds and can retain moisture and/or nutritional components. Examples of characteristics for soils that may be desirable in certain embodiments can be found, for instance, in U.S. Pat. Nos. 3,932,166 and 4,707,176. Synthetic plant cultivation media are also well known in the art and may, in certain embodiments, comprise polymers or hydrogels. Examples of such compositions are described, for example, in U.S. Pat. No. 4,241,537.

Another aspect of the invention relates to a tissue culture of regenerable cells of the wheat cultivar BZ9S09-0133W, as well as plants regenerated therefrom, wherein the regenerated wheat plant is capable of expressing all the morphological and physiological characteristics of a plant grown from the wheat seed designated BZ9S09-0133W.

Yet another aspect of the current invention is a wheat plant of the wheat cultivar BZ9S09-0133W further comprising a single locus conversion. In one embodiment, the wheat plant is defined as comprising the single locus conversion and otherwise capable of expressing all of the morphological and physiological characteristics of the wheat cultivar BZ9S09-0133W. In particular embodiments of the invention, the single locus conversion may comprise a transgenic gene which has been introduced by genetic transformation into the wheat cultivar BZ9S09-0133W or a progenitor thereof. In still other embodiments of the invention, the single locus conversion may comprise a dominant or recessive allele. The locus conversion may confer potentially any trait upon the single locus converted plant, including, but not limited to, herbicide resistance, insect resistance, resistance to bacterial, fungal, or viral disease, male fertility or sterility, and improved nutritional quality.

Still yet another aspect of the invention relates to a first generation ($F_1$) hybrid wheat seed produced by crossing a plant of the wheat cultivar BZ9S09-0133W to a second wheat plant. Also included in the invention are the $F_1$ hybrid wheat plants grown from the hybrid seed produced by crossing the wheat cultivar BZ9S09-0133W to a second wheat plant. Still further included in the invention are the seeds of an $F_1$ hybrid plant produced with the wheat cultivar BZ9S09-0133W as one parent, the second generation ($F_2$) hybrid wheat plant grown from the seed of the $F_1$ hybrid plant, and the seeds of the $F_2$ hybrid plant.

Still yet another aspect of the invention is a method of producing wheat seeds comprising crossing a plant of the wheat cultivar BZ9S09-0133W to any second wheat plant, including itself or another plant of the cultivar BZ9S09-0133W. In particular embodiments of the invention, the method of crossing comprises the steps of: (a) planting seeds of the wheat cultivar BZ9S09-0133W; (b) cultivating wheat plants resulting from said seeds until said plants bear flowers; (c) allowing fertilization of the flowers of said plants; and (d) harvesting seeds produced from said plants.

Still yet another aspect of the invention is a method of producing hybrid wheat seeds comprising crossing the wheat cultivar BZ9S09-0133W to a second, distinct wheat plant that is nonisogenic to the wheat cultivar BZ9S09-0133W. In particular embodiments of the invention, the crossing comprises the steps of: (a) planting seeds of wheat cultivar BZ9S09-0133W and a second, distinct wheat plant, (b) cultivating the wheat plants grown from the seeds until the plants bear flowers; (c) cross pollinating a flower on one of the two plants with the pollen of the other plant, and (d) harvesting the seeds resulting from the cross pollinating.

Still yet another aspect of the invention is a method for developing a wheat plant in a wheat breeding program comprising: (a) obtaining a wheat plant, or its parts, of the cultivar BZ9S09-0133W; and (b) employing said plant or parts as a source of breeding material using plant breeding techniques. In the method, the plant breeding techniques may be selected from the group consisting of recurrent selection, mass selection, bulk selection, backcrossing, pedigree breeding, genetic marker-assisted selection and genetic transformation. In certain embodiments of the invention, the wheat plant of cultivar BZ9S09-0133W may be used as the male or female parent.

Still yet another aspect of the invention is a method of producing a wheat plant derived from the wheat cultivar BZ9S09-0133W, the method comprising the steps of: (a) preparing a progeny plant derived from wheat cultivar BZ9S09-0133W by crossing a plant of the wheat cultivar BZ9S09-0133W with a second wheat plant; and (b) crossing the progeny plant with itself or a second plant to produce a progeny plant of a subsequent generation which is derived from a plant of the wheat cultivar BZ9S09-0133W. In one embodiment of the invention, the method further comprises: (c) crossing the progeny plant of a subsequent generation with itself or a second plant; and (d) repeating steps (b) and (c) for, in some embodiments, at least 2, 3, 4 or more additional generations to produce an inbred wheat plant derived from the wheat cultivar BZ9S09-0133W. Also provided by the invention is a plant produced by this and the other methods of the invention.

In another embodiment of the invention, the method of producing a wheat plant derived from the wheat cultivar BZ9S09-0133W further comprises: (a) crossing the wheat cultivar BZ9S09-0133W-derived wheat plant with itself or another wheat plant to yield additional wheat cultivar BZ9S09-0133W-derived progeny wheat seed; (b) growing the progeny wheat seed of step (a) under plant growth conditions to yield additional wheat cultivar BZ9S09-0133W-derived wheat plants; and (c) repeating the crossing and growing steps of (a) and (b) to generate further wheat cultivar BZ9S09-0133W-derived wheat plants. In specific embodiments, steps (a) and (b) may be repeated at least 1, 2, 3, 4, or 5 or more times as desired. The invention still further provides a wheat plant produced by this and the foregoing methods.

DETAILED DESCRIPTION OF THE INVENTION

Reference now will be made in detail to the embodiments of the invention, one or more examples of which are set forth below. Each example is provided by way of explanation of the invention, not a limitation of the invention. It will be apparent to those skilled in the art that various modifications and variations may be made in the present invention without departing from the scope or spirit of the invention. For instance, features illustrated or described as part of one embodiment, can be used on another embodiment to yield a still further embodiment.

Thus, it is intended that the present invention covers such modifications and variations as come within the scope of the appended claims and their equivalents. Other objects, features, and aspects of the present invention are disclosed in or are obvious from the following detailed description. It is to be understood by one of ordinary skill in the art that the present discussion is a description of exemplary embodiments only, and is not intended as limiting the broader aspects of the present invention In an embodiment, the invention is directed to wheat cultivar BZ9S09-0133W, its seeds, plants, and hybrids. Wheat cultivar BZ9S09-0133W is a hard white spring type common wheat bred for fall planting in the hard white spring wheat growing regions of the United States. The primary usage of wheat cultivar BZ9S09-0133W will be for production of grain, but it can also be used for production of silage harvested in the soft dough stage. The breeding history of the cultivar can be summarized as follows:

WB7328 (BZ9S09-0133W) was selected by Monsanto, from the cross 'Snow-crest*6/Expresso'. The final cross was made in the greenhouse near Bozeman, Mont. in July 2007. The $F_1$ was planted in September 2007 in the greenhouse near Bozeman and the $F_2$ seed harvested in November and then planted near Yuma, Ariz. the same month. $F_3$ heads were selected from agronomically desirable plants in April 2008, bulked, and $F_4$ seed was planted near Bozeman in May 2008. $F_4$ heads were selected from agronomically desirable plants in September and planted as $F_5$ rows in Yuma, Ariz. Agronomically desirable rows were selected in April 2009. Seed from these rows were analyzed for hard spring wheat quality traits, i.e., % protein, test weight, and Sodium Dodecyl Sulfate (SDS) Sedimentation (an indicator of gluten strength). One such row was selected to advance to yield trials and was given the designation BZ9S09-0133W.

BZ9S09-0133W was tested in Monsanto trials in 2009 through 2012 ($F_5$—$F_8$ generations). Leaf tissue samples were collected from the $F_6$ plot and the samples were analyzed for the presence of the stripe rust resistant genes, Yr15 and Yr17. Individual heads were taken from an $F_6$ plot near Bozeman in September 2011 and planted as single rows near Bozeman in May 2012. Individual $F_7$ rows were harvested in September 2012. This seed was used to plant $F_8$ line row plots in November 2012 near Yuma, Ariz. Seven of the plots looked uniform were harvested individually in April 2013. The uniform lines were examined for seed purity and bulked to produce Pre-Breeder seed. The Pre-Breeder seed was planted near Moses Lake, Wash. in May 2013 and the resultant seed was harvested as Breeder Seed in August, 2013. Breeder seed was planted in March 2014 near Warden, Wash. to produce Foundation seed. The Foundation seed was harvested in August 2014. The first anticipated unencumbered sale will be in March 2015.

A variant similar to BZ9S09-0133W but 10-15 cm taller occurs at a frequency of 0.2% (20 plants per 10,000). A red seed variant may occur at a frequency of up to 0.5% (50 seeds per 10,000). An awnless variant may occur at a frequency of 0.02% (2 plant per 10,000). A bronze head variant may occur at a frequency of 0.02% (2/10,000). Otherwise, this cultivar has been uniform and stable in appearance and performance across several generations ($F_5$-$F_{10}$) and environments.

In accordance with another aspect of the invention, there is provided a wheat plant having the morphological and physiological characteristics of BZ9S09-0133W as presented in Table 1. Those of skill in the art will recognize that these are typical values that may vary due to environment and that other values that are substantially equivalent are within the scope of the invention.

TABLE 1

Phenotypic Description of Wheat cultivar BZ9S09-0133W

| CHARACTERISTIC | VALUES/RATINGS |
|---|---|
| 1. PLANT | |
| Coleoptile anthocyanin | Absent |
| Juvenile plant growth | Semi-erect |
| Plant color at boot stage | Green |
| Flag leaf at boot stage: | |
| Orientation | Erect |
| Waxy Bloom | Wax Absent |
| Days to Heading (Julian Date) | 180 |

TABLE 1-continued

Phenotypic Description of Wheat cultivar BZ9S09-0133W

| | CHARACTERISTIC | VALUES/RATINGS |
|---|---|---|
| | Anther Color | Yellow |
| | Plant height (cm) | 73.7 |
| 2. | STEM | |
| | Anthocyanin | Absent |
| | Waxy Bloom | Present |
| | Internode: | |
| | Form | Semi-Solid |
| | Number | 3 |
| | Hairiness of last internode of rachis | Present |
| | Peduncle: | |
| | Form | Erect |
| | Length (cm) | 12.4 |
| | Auricle: | |
| | Anthocyanin | Present |
| | Hair | Present |
| 3. | HEAD (at maturity) | |
| | Density | Lax |
| | Shape | Tapering |
| | Curvature | Erect |
| | Awnedness | Awned |
| 4. | GLUMES (at maturity) | |
| | Color | White |
| | Shoulder | Square |
| | Shoulder width | Narrow |
| | Beak shape | Acute |
| | Beak width | Narrow |
| | Glume length | Medium (ca. 8 mm) |
| | Glume width | Narrow (ca. 3 mm) |
| | Pubescence | Not Present |
| 5. | SEED | |
| | Shape | Ovate |
| | Cheek | Angular |
| | Brush | Medium |
| | Brush collar | Not Collared |
| | Crease width | Wide |
| | Crease depth | Deep |
| | Color | White |
| | Texture | Hard |
| | Seed weight (g/1000 kernels) | 33 |
| | Germ size | Midsize |
| 6. | DISEASE REACTIONS | |
| | *Puccinia striiformis* (Stripe rust): | Resistant |

In an embodiment, the invention provides a composition comprising a seed of BZ9S09-0133W comprised in plant seed growth media. Advantageously, plant seed growth media can provide adequate physical support for seeds and can retain moisture and/or nutritional components. In certain embodiments, the plant seed growth media is a soil or synthetic cultivation medium. Any plant seed growth media known in the art may be utilized in this embodiment and the invention is in no way limited to soil or synthetic cultivation medium. Examples of characteristics for soils that may be desirable in certain embodiments can be found, for instance, in U.S. Pat. Nos. 3,932,166 and 4,707,176. Plant cultivation media are well known in the art and may, in certain embodiments, comprise polymers, hydrogels, or the like. Examples of such compositions are described, for example, in U.S. Pat. No. 4,241,537. In specific embodiments, the growth medium may be comprised in a container or may, for example, be soil in a field.

In another embodiment, the invention is directed to methods for producing a wheat plant by crossing a first parent wheat plant with a second parent wheat plant, wherein the first or second wheat plant is the wheat plant from the cultivar BZ9S09-0133W. In an embodiment, the first and second parent wheat plants may be from the cultivar BZ9S09-0133W (i.e., self-pollination). Any methods using the cultivar BZ9S09-0133W are part of this invention: selfing, backcrosses, hybrid breeding, and crosses to populations. Any plants produced using cultivar BZ9S09-0133W as a parent are within the scope of this invention. In certain embodiments, the invention is also directed to cells that, upon growth and differentiation, produce a cultivar having essentially all of the morphological and physiological characteristics of BZ9S09-0133W. The present invention additionally contemplates, in various embodiments, a wheat plant regenerated from a tissue culture of cultivar BZ9S09-0133W.

In some embodiments of the invention, the invention is directed to a transgenic variant of BZ9S09-0133W. A transgenic variant of BZ9S09-0133W may contain at least one transgene but could contain at least 1, 2, 3, 4, 5, 6, 7, 8, 9, 10, or more transgenes. In another embodiment, a transgenic variant of BZ9S09-0133W may contain no more than 15, 14, 13, 12, 11, 10, 9, 8, 7, 6, 5, 4, 3, or 2 transgenes. Another embodiment of the invention involves a process for producing wheat cultivar BZ9S09-0133W further comprising a desired trait, said process comprising introducing a transgene that confers a desired trait to a wheat plant of cultivar BZ9S09-0133W. Methods for producing transgenic plants have been developed and are well known in the art. As part of the invention, one of ordinary skill in the art may utilize any method of producing transgenic plants which is currently known or yet to be developed.

Numerous methods for plant transformation have been developed, including biological and physical plant transformation protocols. In addition, expression vectors and in vitro culture methods for plant cell or tissue transformation and regeneration of plants are available.

In certain embodiments, the desired trait may be one or more of herbicide tolerance or resistance, insect resistance or tolerance, disease resistance or tolerance, resistance for bacterial, viral, or fungal disease, male fertility, male sterility, decreased phytate, or modified fatty acid or carbohydrate metabolism. The specific transgene may be any known in the art or listed herein, including, but not limited to a polynucleotide conferring resistance to imidazolinone, dicamba, sulfonylurea, glyphosate, glufosinate, triazine, benzonitrile, cyclohexanedione, phenoxy propionic acid, and L-phosphinothricin; a polynucleotide encoding a *Bacillus thuringiensis* polypeptide, a polynucleotide encoding phytase, FAD-2, FAD-3, galactinol synthase or a raffinose synthetic enzyme, *Fusarium, Septoria*, or various viruses or bacteria.

Various genetic elements can be introduced into the plant genome using transformation. These elements include, but are not limited to, genes, coding sequences, inducible, constitutive, and tissue-specific promoters, enhancing sequences, and signal and targeting sequences.

In some embodiments, the invention comprises a BZ9S09-0133W plant that has been developed using both genetic engineering and traditional breeding techniques. For example, a genetic trait may have been engineered into the genome of a particular wheat plant may then be moved into the genome of a BZ9S09-0133W plant using traditional breeding techniques that are well known in the plant breeding arts. Likewise, a genetic trait that has been engineered into the genome of a BZ9S09-0133W wheat plant may then be moved into the genome of another cultivar using traditional breeding techniques that are well known in the plant breeding arts. A backcrossing approach is commonly used to move a transgene or transgenes from a transformed wheat cultivar into an already developed wheat cultivar, and the resulting backcross conversion plant would then comprise the transgene(s).

Plant transformation involves the construction of an expression vector that will function in plant cells. Such a vector may comprise DNA comprising a gene under control of or operatively linked to a regulatory element (for example, a promoter). The expression vector may contain one or more such operably linked gene/regulatory element combinations. The vector(s) may be in the form of a plasmid and can be used alone or in combination with other plasmids to provide transformed wheat plants, using transformation methods as described below to incorporate transgenes into the genetic material of the wheat plant(s).

Expression Vectors for Wheat Transformation: Marker Genes

Expression vectors may include at least one genetic marker operably linked to a regulatory element that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and may include, for example, genes that code for enzymes that metabolically detoxify a selective chemical agent, which may be an antibiotic or an herbicide, or genes that encode an altered target which is insensitive to the inhibitor. Positive selection methods are also known in the art.

One commonly used selectable marker gene for plant transformation is the neomycin phosphotransferase II (nptII) gene, which when under the control of plant regulatory signals, confers resistance to kanamycin. Another commonly used selectable marker gene is the hygromycin phosphotransferase gene, which confers resistance to the antibiotic hygromycin.

Additional selectable marker genes of bacterial origin that confer resistance to antibiotics include gentamycin acetyl transferase, streptomycin phosphotransferase, and aminoglycoside-3'-adenyl transferase, the bleomycin resistance determinant. Other selectable marker genes confer tolerance or resistance to herbicides such as glyphosate, glufosinate, or bromoxynil, or the like.

Other selectable marker genes for plant transformation that are not of bacterial origin may include, for example, mouse dihydrofolate reductase, plant 5-enolpyruvylshikimate-3-phosphate synthase, and plant acetolactate synthase.

Another class of marker genes for plant transformation requires screening of presumptively transformed plant cells, rather than direct genetic selection of transformed cells, for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase, and chloramphenicol acetyltransferase. In vivo methods for visualizing GUS activity that do not require destruction of plant tissue are also available. More recently, a gene encoding Green Fluorescent Protein (GFP) has been utilized as a marker for gene expression in prokaryotic and eukaryotic cells. GFP and mutants of GFP may also be used as screenable markers.

Expression Vectors for Wheat Transformation: Promoters

Genes included in expression vectors must be driven by a nucleotide sequence comprising a regulatory element, for example, a promoter. Many types of promoters are well known in the transformation arts, as are other regulatory elements that can be used alone or in combination with promoters.

As used herein, "promoter" includes reference to a region of DNA upstream of the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters may be referred to as "tissue-preferred." Promoters that initiate transcription only in certain tissue are referred to as "tissue-specific." A "cell type" specific promoter primarily drives expression in certain cell types in one or more organs, for example, vascular cells in roots or leaves. An "inducible" promoter is a promoter under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive" promoter is a promoter that is active under most environmental conditions.

A. Inducible Promoters—An inducible promoter is operably linked to a gene for expression in wheat. Optionally, the inducible promoter may be operably linked to a nucleotide sequence encoding a signal sequence that is operably linked to a gene for expression in wheat. With an inducible promoter, the rate of transcription increases in response to an inducing agent.

Any inducible promoter may be used in the present invention. Exemplary inducible promoters include, but are not limited to, those from the ACEI system, which respond to copper, and the In2 gene from maize, which responds to benzene-sulfonamide herbicide safeners. In an embodiment, the inducible promoter may be a promoter that responds to an inducing agent to which plants do not normally respond. An exemplary inducible promoter may be an inducible promoter from a steroid hormone gene, the transcriptional activity of which is induced by a glucocorticosteroid hormone.

B. Constitutive Promoters—A constitutive promoter is operably linked to a gene for expression in wheat, or is operably linked to a nucleotide sequence encoding a signal sequence that is operably linked to a gene for expression in wheat.

Many different constitutive promoters can be utilized in the present invention. Exemplary constitutive promoters include, but are not limited to, the promoters from plant viruses, such as the 35S promoter from CaMV and the promoters from such genes as rice actin; ubiquitin; pEMU; MAS, and maize H3 histone. The ALS promoter, Xbal/NcoI fragment 5' to the *Brassica napus* ALS3 structural gene (or a nucleotide sequence similarity to said Xbal/NcoI fragment), represents a particularly useful constitutive promoter.

C. Tissue-specific or Tissue-preferred Promoters—A tissue-specific promoter is operably linked to a gene for expression in wheat. The tissue-specific promoter may be operably linked to a nucleotide sequence encoding a signal sequence that is operably linked to a gene for expression in wheat. Plants transformed with a gene of interest operably linked to a tissue-specific promoter may produce the protein product of the transgene exclusively, or preferentially, in a specific tissue.

Any tissue-specific or tissue-preferred promoter can be utilized in the present invention. Exemplary tissue-specific or tissue-preferred promoters include, but are not limited to, a root-preferred promoter, such as that from the phaseolin gene; a leaf-specific and light-induced promoter, such as that from cab or rubisco; an anther-specific promoter, such as that from LAT52; a pollen-specific promoter, such as that from Zml 3; or a microspore-preferred promoter, such as that from apg.

Signal Sequences for Targeting Proteins to Subcellular Compartments

Transport of protein produced by transgenes to a subcellular compartment such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized. The presence of a signal sequence directs a polypeptide to either an intracellular organelle or subcellular compartment or for secretion to the apoplast. Many signal sequences are known in the art.

Foreign Protein Genes and Agronomic Genes

Using transgenic plants according to the present invention, a foreign protein can be produced in commercial quantities. Thus, techniques for the selection and propagation of transformed plants, which are well understood in the art, yield a plurality of transgenic plants that may be harvested in a conventional manner. A foreign protein can then be extracted from a tissue of interest or from total biomass. Protein extraction from plant biomass can be accomplished by known methods.

According to an embodiment of the invention, the transgenic plant provided for commercial production of foreign protein is, or is derived from a BZ9S09-0133W wheat plant. In another embodiment, the biomass of interest is or is derived from a BZ9S09-0133W seed. For the relatively small number of transgenic plants that show higher levels of expression, a genetic map can be generated, primarily via conventional restriction fragment length polymorphism (RFLP), polymerase chain reaction (PCR), and simple sequence repeat (SSR) analysis, which identify the approximate chromosomal location of the integrated DNA molecule. Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR, and sequencing, all of which are conventional techniques well known in the art.

In certain embodiments, the invention comprises transformed BZ9S09-0133W plants that express particular agronomic genes or phenotypes of agronomic interest. Exemplary genes implicated in this regard include, but are not limited to, those categorized below:

1. Genes that Confer Tolerance or Resistance to Pests or Disease and that Encode:

A. Plant disease tolerance or resistance genes. Plant defenses are often activated by specific interaction between the product of a disease tolerance or resistance gene (R) in the plant and the product of a corresponding avirulence (Avr) gene in the pathogen. A plant variety can be transformed with one or more cloned resistance genes to engineer plants that are resistant to specific pathogen strains.

B. A gene conferring resistance to a pest, such as nematodes.

C. A *Bacillus thuringiensis* protein, a derivative thereof, or a synthetic polypeptide modeled thereon. Moreover, DNA molecules encoding δ-endotoxin genes can be purchased from American Type Culture Collection, Manassas, Va., for example, under ATCC Accession Nos. 40098, 67136, 31995 and 31998.

D. A lectin. The nucleotide sequence of several *Clivia miniata* mannose-binding lectin genes are known in the art.

E. A vitamin-binding protein such as avidin or avidin homologues.

F. An enzyme inhibitor, for example, a protease or proteinase inhibitor or an amylase inhibitor. For example, the nucleotide sequences of rice cysteine proteinase inhibitor, cDNA encoding tobacco proteinase inhibitor I, and *Streptomyces nitrosporeus* α-amylase inhibitor are known in the art.

G. An insect-specific hormone or pheromone such as an ecdysteroid and juvenile hormone, a variant thereof, a mimetic based thereon, or an antagonist or agonist thereof. For example, the baculovirus expression of cloned juvenile hormone esterase, an inactivator of juvenile hormone, is known in the art.

H. An insect-specific peptide or neuropeptide which, upon expression, disrupts the physiology of the affected pest. For example, it is known that expression cloning yields DNA coding for insect diuretic hormone receptor and an allostatin can be identified in *Diploptera puntata*. Genes encoding insect-specific, paralytic neurotoxins are also known in the art.

I. An insect-specific venom produced in nature by a snake, a wasp, etc. For example, heterologous expression in plants of a gene coding for a scorpion insectotoxic peptide is known in the art.

J. An enzyme responsible for a hyper-accumulation of a monoterpene, a sesquiterpene, a steroid, a hydroxamic acid, a phenylpropanoid derivative, or another non-protein molecule with insecticidal activity.

K. An enzyme involved in the modification, including the post-translational modification, of a biologically active molecule. For example, such enzymes include, but are not limited to, a glycolytic enzyme, a proteolytic enzyme, a lipolytic enzyme, a nuclease, a cyclase, a callase, a transaminase, an esterase, a hydrolase, a phosphatase, a kinase, a phosphorylase, a polymerase, an elastase, a chitinase, and a glucanase, whether natural or synthetic. DNA molecules that contain chitinase-encoding sequences can be obtained, for example, from the ATCC under Accession Nos. 39637 and 67152. The nucleotide sequences of a cDNA encoding tobacco hookworm chitinase and parsley ubi4-2 polyubiquitin gene are also known in the art.

L. A molecule that stimulates signal transduction. For example, the nucleotide sequences for mung bean calmodulin cDNA clones and a maize calmodulin cDNA clone are known in the art.

M. A hydrophobic moment peptide. For example, peptide derivatives of Tachyplesin, which inhibit fungal plant pathogens, or synthetic antimicrobial peptides that confer disease resistance.

N. A membrane permease, a channel former, or a channel blocker. For example, heterologous expression of a cecropin-13 lytic peptide analog to render transgenic tobacco plants resistant to *Pseudomonas solanacearum* is known in the art.

O. A viral-invasive protein or a complex toxin derived therefrom. For example, the accumulation of viral coat proteins in transformed plant cells imparts resistance to viral infection and/or disease development affected by the virus from which the coat protein gene is derived, as well as by related viruses. Coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus.

P. An insect-specific antibody or an immunotoxin derived therefrom. Thus, an antibody targeted to a critical metabolic function in the insect gut would inactivate an affected enzyme, killing the insect. For example, enzymatic inactivation in transgenic tobacco via production of single-chain antibody fragments is known in the art.

Q. A virus-specific antibody. For example, it is known in the art that transgenic plants expressing recombinant antibody genes are protected from virus attack.

R. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. The cloning and characterization of a gene that encodes a bean endopolygalacturonase-inhibiting protein is known in the art.

S. A developmental-arrestive protein produced in nature by a plant. For example, it has been shown that transgenic plants expressing the barley ribosome-inactivating gene have an increased resistance to fungal disease.

T. Genes expressing proteins with antifungal action. *Fusarium* head blight along with deoxynivalenol both produced by the pathogen *Fusarium graminearum* (Schwabe) have caused devastating losses in wheat production. Genes expressing proteins with antifungal action can be used as transgenes to prevent *Fusarium* head blight. Various classes of proteins have been identified. Examples include endochitinases, exochitinases, glucanases, thionins, thaumatin-like proteins, osmotins, ribosome-inactivating proteins, flavonoids, and lactoferricin. During infection with *Fusarium graminearum*, deoxynivalenol is produced. There is evidence that production of deoxynivalenol increases the virulence of the disease. Genes with properties for detoxification of deoxynivalenol have been engineered for use in wheat. A synthetic peptide that competes with deoxynivalenol has been identified. Changing the ribosomes of the host so that they have reduced affinity for deoxynivalenol has also been used to reduce the virulence of *Fusarium graminearum*. Genes used to help reduce *Fusarium* head blight include, but are not limited to, Tri101 (*Fusarium*), PDR5 (yeast), tlp-1 (oat), tlp-2 (oat), leaf tlp-1 (wheat), tlp (rice), tlp-4 (oat), endochitinase, exochitinase, glucanase (*Fusarium*), permatin (oat), seed hordothionin (barley), alpha-thionin (wheat), acid glucanase (alfalfa), chitinase (barley and rice), class beta II-1,3-glucanase (barley), PR5/tlp (*Arabidopsis*), zeamatin (maize), type 1 RIP (barley), NPR1 (*Arabidopsis*), lactoferrin (mammal), oxalylCoA-decarboxylase (bacterium), IAP (baculovirus), ced-9 (*C. elegans*), and glucanase (rice and barley).

U. A gene, for example, the H9, H10, and H21 genes, conferring resistance to a pest, such as Hessian fly, stem soft fly, cereal leaf beetle, and/or green bug.

V. A gene conferring resistance to diseases such as wheat rusts, *Septoria tritici*, *Septoria nodorum*, powdery mildew, *Helminthosporium* diseases, smuts, bunts, *Fusarium* diseases, bacterial diseases, and viral diseases.

W. Genes involved in the Systemic Acquired Resistance (SAR) response and/or the pathogenesis-related genes.

X. Antifungal genes.

Y Detoxification genes, such as for fumonisin, beauvericin, moniliformin, and zearalenone and their structurally related derivatives.

Z. Cystatin and cysteine proteinase inhibitors.

AA. Defensin genes.

BB. Genes conferring resistance to nematodes.

2. Genes that Confer Tolerance or Resistance to an Herbicide:

A. An herbicide that inhibits the growing point or meristem, such as an imidazolinone or a sulfonylurea. Exemplary genes in this category code for mutant ALS and AHAS enzyme.

B. Glyphosate (resistance conferred by mutant 5-enolpyruvylshikimate-3-phosphate synthase (EPSPS) and aroA genes) and other phosphono compounds, such as glufosinate (phosphinothricin acetyl transferase (PAT) and *Streptomyces hygroscopicus* PAT bar genes), and pyridinoxy or phenoxy propionic acids and cyclohexanediones (ACCase inhibitor-encoding genes). For example, the nucleotide sequence of a form of EPSP which can confer glyphosate resistance is known in the art. A DNA molecule encoding a mutant aroA gene can be obtained under ATCC accession number 39256, and the nucleotide sequence of the mutant gene is known. Nucleotide sequences of glutamine synthetase genes that confer tolerance or resistance to herbicides such as L-phosphinothricin are also known in the art. The nucleotide sequence of a PAT gene is known in the art, as is the production of transgenic plants that express chimeric bar genes coding for PAT activity. Exemplary genes conferring resistance to phenoxy propionic acids and cyclohexanediones, such as sethoxydim and haloxyfop are the Accl-S1, Accl-S2, and Accl-S3 genes.

C. An herbicide that inhibits photosynthesis, such as a triazine (psbA and gs+ genes) or a benzonitrile (nitrilase gene). Nucleotide sequences for nitrilase genes are disclosed and DNA molecules containing these genes are available under ATCC Accession Nos. 53435, 67441, and 67442. Cloning and expression of DNA coding for a glutathione S-transferase is described in the art.

D. Acetohydroxy acid synthase. This enzyme has been found to make plants that express this enzyme tolerant or resistant to multiple types of herbicides and has been introduced into a variety of plants. Other genes that confer tolerance or resistance to herbicides include a gene encoding a chimeric protein of rat cytochrome P4507A1 and yeast NADPH-cytochrome P450 oxidoreductase, genes for glutathione reductase and superoxide dismutase, and genes for various phosphotransferases.

E. Protoporphyrinogen oxidase (protox). Protox is necessary for the production of chlorophyll, which is necessary for survival in all plants. The protox enzyme serves as the target for a variety of herbicidal compounds. These herbicides also inhibit growth of different species of plants present, causing their total destruction. The development of plants containing altered protox activity that are tolerant or resistant to these herbicides is described in the art.

3. Genes that Confer or Contribute to a Value-Added Trait, Such as:

A. Modified fatty acid metabolism, for example, by transforming a plant with an antisense gene of stearyl-ACP desaturase to increase stearic acid content of the plant.

B. Decreased phytate content. This can be accomplished by: (1) Introduction of a phytase-encoding gene that enhances breakdown of phytate, adding more free phosphate to the transformed plant; or (2) Up-regulation of a gene that reduces phytate content. For example, the nucleotide sequence of an *Aspergillus niger* phytase gene has been described in the art.

C. Modified carbohydrate composition effected, for example, by transforming plants with a gene coding for an enzyme that alters the branching pattern of starch, or, a gene altering thioredoxin such as NTR and/or TRX and/or a gamma zein knockout or mutant, such as cs27, TUSC27, or en27. For example, the nucleotide sequences of *Streptococcus nutans* fructosyltransferase gene, *Bacillus subtilis* levansucrase gene, and tomato invertase genes are known in the art. Transgenic plants can be produced that express *Bacillus licheniformis* alpha-amylase, that site-direct mutagenesis of barley alpha-amylase gene, or confer maize endosperm starch branching enzyme II or improved digestibility and/or starch extraction through modification of UDP-D-xylose 4-epimerase. Methods of producing high oil seed by modification of starch levels (AGP) are also known. The fatty acid modification genes mentioned above may also be used to affect starch content and/or composition through the interrelationship of the starch and oil pathways.

D. Elevated oleic acid via FAD-2 gene modification and/or decreased linolenic acid via FAD-3 gene modification.

E. Altering conjugated linolenic or linoleic acid content, or LEC 1, AGP, Dekl, Superall, milps, various Ipa genes such as Ipa1, Ipa3, hpt, or hggt.

F. Altered antioxidant content or composition, such as alteration of tocopherol or tocotrienols. For example, manipulation of antioxidant levels through alteration of a phytl prenyl transferase (ppt) is known, as is manipulation of antioxidant levels through alteration of a homogentisate geranyl geranyl transferase (hggt).

G. The content of high-molecular weight gluten subunits (HMS-GS). Genomic clones have been isolated for different subunits. For example, genomic clones have transformed wheat with genes that encode a modified HMW-GS.

H. Increased protein metabolism, zinc and iron content, for example, by regulating the NAC gene, increasing protein metabolism by regulating the Gpc-B1 gene, or regulating glutenin and gliadin genes.

I. Altered essential seed amino acids. Methods of increasing accumulation of essential amino acids in seeds, binary methods of increasing accumulation of essential amino acids in seeds, alteration of amino acid compositions in seeds, methods for altering amino acid content of proteins, alteration of amino acid compositions in seeds, and proteins with enhanced levels of essential amino acids all are known in the art. Other examples may include high methionine, high threonine, plant amino acid biosynthetic enzymes, increased lysine and threonine, plant tryptophan synthase beta subunit, methionine metabolic enzymes, high sulfur, increased methionine, plant amino acid biosynthetic enzymes, engineered seed protein having higher percentage of essential amino acids, increased lysine, increasing sulfur amino acid content, synthetic storage proteins with defined structure containing programmable levels of essential amino acids for improvement of the nutritional value of plants, increased threonine, increased lysine, Ces A: cellulose synthase, hemicellulose, UDPGdH, and RGP.

4. Genes that Control Male Sterility

There are several methods of conferring genetic male sterility available, such as multiple mutant genes at separate locations within the genome that confer male sterility. In addition to these methods, a system of nuclear male sterility that includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on", resulting in the male fertility gene not being transcribed, is known. Fertility is restored by inducing, or turning "on", the promoter, which in turn allows the gene that confers male fertility to be transcribed.

A. Introduction of a deacetylase gene under the control of a tapetum-specific promoter and with the application of the chemical N-Ac-PPT.

B. Introduction of various stamen-specific promoters.

C. Introduction of the barnase and the barstar genes.

5. Genes that Create a Site for Site Specific DNA Integration.

This includes the introduction of FRT sites that may be used in the FLP/FRT system and/or Lox sites that may be used in the Cre/Loxp system. Other systems that may be used include the Gin recombinase of phage Mu, the Pin recombinase of *E. coli*, and the R/RS system of the pSR1 plasmid.

6. Genes that Affect Abiotic Stress Resistance.

A. Genes that affect abiotic stress resistance (including but not limited to flowering, seed development, enhancement of nitrogen utilization efficiency, altered nitrogen responsiveness, drought resistance or tolerance, cold resistance or tolerance, and salt resistance or tolerance) and increased yield under stress. For example, water use efficiency can be altered through alteration of malate. In addition, various genes, including CBF genes and transcription factors, can be effective in mitigating the negative effects of freezing, high salinity, and drought on plants, as well as conferring other positive effects on plant phenotype. Abscisic acid can be altered in plants, resulting in improved plant phenotype, such as increased yield and/or increased tolerance to abiotic stress. Cytokinin expression can be modified resulting in plants with increased stress tolerance, such as drought tolerance, and/or increased yield. Nitrogen utilization can be enhanced and/or nitrogen responsiveness can be altered. Ethylene can be altered. Plant transcription factors or transcriptional regulators of abiotic stress can also be altered.

B. Improved tolerance to water stress from drought or high salt water condition. The HVA1 protein belongs to the group 3 LEA proteins that include other members such as wheat pMA2005, cotton D-7, carrot Dc3, and rape pLEA76. These proteins are characterized by 11-mer tandem repeats of amino acid domains which may form a probable amphophilic alpha-helical structure that presents a hydrophilic surface with a hydrophobic stripe. The barley HVA1 gene and the wheat pMA2005 gene are highly similar at both the nucleotide level and predicted amino acid level. These two monocot genes are closely related to the cotton D-7 gene and carrot Dc3 gene with which they share a similar structural gene organization. There is, therefore, a correlation between LEA gene expression or LEA protein accumulation with stress tolerance in a number of plants. For example, in severely dehydrated wheat seedlings, the accumulation of high levels of group 3 LEA proteins was correlated with tissue dehydration tolerance. Studies on several Indica varieties of rice showed that the levels of group 2 LEA proteins (also known as dehydrins) and group 3 LEA proteins in roots were significantly higher in salt-tolerant varieties compared with sensitive varieties. The barley HVA1 gene was transformed into wheat. Transformed wheat plants showed increased tolerance to water stress.

C. Improved water stress tolerance through increased mannitol levels via the bacterial mannitol-1-phosphate dehydrogenase gene. It is known to produce a plant with a genetic basis for coping with water deficit by introduction of the bacterial mannitol-1-phosphate dehydrogenase gene, mt1D, into tobacco cells via *Agrobacterium*-mediated transformation. Root and leaf tissues from transgenic plants regenerated from these transformed tobacco cells contained up to 100 mM mannitol. Control plants contained no detectable mannitol. To determine whether the transgenic tobacco plants exhibited increased tolerance to water deficit, the growth of transgenic plants was compared to that of untransformed control plants in the presence of 250 mM NaCl. After 30 days of exposure to 250 mM NaCl, transgenic plants had decreased weight loss and increased height relative to their untransformed counterparts. The authors concluded that the presence of mannitol in these transformed tobacco plants contributed to water deficit tolerance at the cellular level.

Other genes and transcription factors that affect plant growth and agronomic traits such as yield, flowering, plant growth and/or plant structure, can be introduced or introgressed into plants.

Methods for Wheat Transformation

Numerous methods for plant transformation have been developed, including biological and physical plant transformation protocols. In addition, expression vectors and in vitro culture methods for plant cell or tissue transformation and regeneration of plants are available.

A. *Agrobacterium*-Mediated Transformation. One method for introducing an expression vector into plants is based on the natural transformation system of *Agrobacterium*. *A. tumefaciens* and *A. rhizogenes* are plant pathogenic soil bacteria that genetically transform plant cells. The Ti and Ri plasmids of *A. tumefaciens* and *A. rhizogenes*, respectively, carry genes responsible for genetic transformation of the plant. Descriptions of *Agrobacterium* vector systems and methods for *Agrobacterium*-mediated gene transfer are well known in the art.

B. Direct Gene Transfer. Several methods of plant transformation, collectively referred to as direct gene transfer, have been developed as an alternative to *Agrobacterium*-mediated transformation. A generally applicable method of plant transformation is microprojectile-mediated transformation, wherein DNA is carried on the surface of microprojectiles measuring 1 to 4 pm. The expression vector is introduced into plant tissues with a biolistic device that accelerates the microprojectiles to speeds of 300 to 600 m/s, which is sufficient to penetrate plant cell walls and membranes.

Another method for physical delivery of DNA to plants is sonication of target cells. Alternatively, liposome and spheroplast fusion have been used to introduce expression vectors into plants. Direct uptake of DNA into protoplasts using $CaCl_2$ precipitation, polyvinyl alcohol or polyL-ornithine has also been reported. Electroporation of protoplasts and whole cells and tissues has also been described. Following transformation of wheat target tissues, expression of the above-described selectable marker genes allows for preferential selection of transformed cells, tissues and/or plants, using regeneration and selection methods that are well known in the art.

The foregoing methods for transformation would typically be used for producing a transgenic variety. The transgenic variety could then be crossed, with another (non-transformed or transformed) variety, in order to produce a new transgenic variety. Alternatively, a genetic trait which has been engineered into a particular wheat cultivar using the foregoing transformation techniques could be moved into another cultivar using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context.

Genetic Marker Profile Through SSR and First Generation Progeny

In addition to phenotypic observations, a plant can also be identified by its genotype. The genotype of a plant can be characterized through a genetic marker profile, which can identify plants of the same variety or a related variety or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as microsatellites, and Single Nucleotide Polymorphisms (SNPs).

Particular markers used for these purposes are not limited to any particular set of markers, but are envisioned to include any type of marker and marker profile that provides a means of distinguishing varieties. One method of comparison is to use only homozygous loci for BZ9S09-0133W.

In addition to being used for identification of wheat cultivar BZ9S09-0133W and plant parts and plant cells of cultivar BZ9S09-0133W, the genetic profile may be used to identify a wheat plant produced through the use of BZ9S09-0133W or to verify a pedigree for progeny plants produced through the use of BZ9S09-0133W. The genetic marker profile is also useful in breeding and developing backcross conversions.

In some embodiments, the present invention comprises a wheat plant characterized by molecular and physiological data obtained from the representative sample of BZ9S09-0133W, deposited with the American Type Culture Collection (ATCC). Provided in further embodiments of the invention is a wheat plant formed by the combination of the BZ9S09-0133W plant or plant cell with another wheat plant or cell and comprising the homozygous alleles of the variety.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR), thereby eliminating the need for labor-intensive Southern hybridization. PCR detection uses two oligonucleotide primers flanking the polymorphic segment of repetitive DNA. Repeated cycles of heat denaturation of the DNA, followed by annealing of the primers to their complementary sequences at low temperatures, and extension of the annealed primers with DNA polymerase, comprise the major part of the methodology.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing varieties, all SSR profiles may be performed in the same lab.

The SSR profile of wheat plant BZ9S09-0133W can be used to identify plants comprising BZ9S09-0133W as a parent, since such plants will comprise the same homozygous alleles as BZ9S09-0133W. Because the wheat cultivar is essentially homozygous at all relevant loci, most loci should have only one type of allele present. In contrast, a genetic marker profile of an F1 progeny should be the sum of those parents, e.g., if one parent was homozygous for allele x at a particular locus, and the other parent homozygous for allele y at that locus, then the F1 progeny will be xy (heterozygous) at that locus. Subsequent generations of progeny produced by selection and breeding are expected to be of genotype x (homozygous), y (homozygous), or xy (heterozygous) for that locus position. When the F1 plant is selfed or sibbed for successive filial generations, the locus should be either x or y for that position.

In addition, plants and plant parts substantially benefiting from the use of BZ9S09-0133W in their development, such as BZ9S09-0133W comprising a backcross conversion, transgene, or genetic sterility factor, may be identified by having a molecular marker profile with a high percent identity to BZ9S09-0133W. In an embodiment, such a percent identity might be 95%, 96%, 97%, 98%, 99%, 99.5% or 99.9% identical to BZ9S09-0133W.

The SSR profile of BZ9S09-0133W also can be used to identify essentially derived varieties and other progeny varieties developed from the use of BZ9S09-0133W, as well as cells and other plant parts thereof. Progeny plants and plant parts produced using BZ9S09-0133W may be identified by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% genetic contribution from BZ9S09-0133W, as measured by either percent identity or percent similarity. Such progeny may be further characterized as being within a pedigree distance of BZ9S09-0133W, such as within 1, 2, 3, 4 or 5 or fewer cross-pollinations to a wheat plant other than BZ9S09-0133W or a plant that has BZ9S09-0133W as a progenitor. Unique molecular profiles may be identified with other molecular tools such as SNPs and RFLPs.

While determining the SSR genetic marker profile of a plant as described above, several unique SSR profiles may also be identified that did not appear in either parent plant. Such unique SSR profiles may arise during the breeding process from recombination or mutation. A combination of several unique alleles provides a means of identifying a plant variety, an F1 progeny produced from such variety, and further progeny produced from such variety.

Gene Conversion

When the term "wheat plant" is used in the context of the present invention, this also includes any gene conversions of that cultivar. Backcrossing methods can be used with the present invention to improve or introduce a characteristic into the cultivar. For example, a variety may be backcrossed 1, 2, 3, 4, 5, 6, 7, 8, 9 or more times to the recurrent parent. The parental wheat plant that contributes the gene for the desired characteristic is termed the "nonrecurrent" or "donor" parent. This terminology refers to the fact that the nonrecurrent parent is used one time in the backcross protocol and therefore does not recur. The parental wheat plant to which the gene or genes from the nonrecurrent parent are transferred is known as the recurrent parent, as it is used for several rounds in the backcrossing protocol. In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a wheat plant is obtained wherein essentially all of the desired morphological and physiological characteristics of the recurrent parent are recovered in the converted plant, in addition to the single transferred gene from the nonrecurrent parent.

The selection of a suitable recurrent parent contributes to a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired morphological and physiological, constitution of the original variety. The choice of the particular nonrecurrent parent will depend on the purpose of the backcross. One of the major purposes is to add commercially desirable, agronomically important traits to the plant. The exact backcrossing protocol will depend on the characteristic or trait being altered. Although backcrossing methods are simplified when the characteristic being transferred is a dominant allele, a recessive allele may also be transferred. In this instance, it may be necessary to introduce a test of the progeny to determine if the desired characteristic has been successfully transferred.

Many single gene traits have been identified that are not regularly selected for in the development of a new variety, but that can be improved by backcrossing techniques. Single gene traits may or may not be transgenic. Examples of these traits include, but are not limited to, male sterility, waxy starch, herbicide tolerance or resistance, resistance for bacterial, fungal, or viral disease, insect resistance or tolerance, male fertility, enhanced nutritional quality, industrial usage, yield stability and yield enhancement. These genes are generally inherited through the nucleus.

Introduction of a New Trait or Locus into BZ9S09-0133W

Cultivar BZ9S09-0133W represents a new base genetic variety into which a new locus or trait may be introgressed. Direct transformation and backcrossing represent two important methods that can be used to accomplish such an introgression. The term backcross conversion and single locus conversion are used interchangeably to designate the product of a backcrossing program.

Backcross Conversions of BZ9S09-0133W

A backcross conversion of BZ9S09-0133W occurs when DNA sequences are introduced through backcrossing, with BZ9S09-0133W utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses, or additional crosses. Molecular marker assisted breeding or selection may be utilized to reduce the number of backcrosses necessary to achieve the backcross conversion. For example, a backcross conversion can be made in as few as two backcrosses.

The complexity of the backcross conversion method depends on the type of trait being transferred (single genes or closely linked genes versus unlinked genes), the level of expression of the trait, the type of inheritance (cytoplasmic or nuclear) and the types of parents included in the cross. It is understood by those of ordinary skill in the art that for single gene traits that are relatively easy to classify, the backcross method is effective and relatively easy to manage. Desired traits that may be transferred through backcross conversion include, but are not limited to, sterility (nuclear and cytoplasmic), fertility restoration, nutritional enhancements, drought tolerance, nitrogen utilization, altered fatty acid profile, low phytate, industrial enhancements, disease resistance or tolerance (bacterial, fungal or viral), insect resistance or tolerance, and herbicide tolerance or resistance. In addition, an introgression site itself, such as an FRT site, Lox site, or other site specific integration site, may be inserted by backcrossing and utilized for direct insertion of one or more genes of interest into a specific plant variety. A single locus may contain several transgenes, such as a transgene for disease resistance that, in the same expression vector, also contains a transgene for herbicide tolerance or resistance. The gene for herbicide tolerance or resistance may be used as a selectable marker and/or as a phenotypic trait. A single locus conversion of site specific integration system allows for the integration of multiple genes at the converted loci.

The backcross conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele requires growing and selling the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype of the recurrent parent. The backcross is a form of inbreeding, and the features of the recurrent parent are automatically recovered after successive backcrosses. Some sources suggest from one to four or more backcrosses, but as noted above, the number of backcrosses necessary can be reduced with the use of molecular markers. Other factors, such as a genetically similar donor parent, may also reduce the number of backcrosses necessary. Backcrossing is easiest for simply inherited, dominant and easily recognized traits.

One process for adding or modifying a trait or locus in wheat cultivar BZ9S09-0133W comprises crossing BZ9S09-0133W plants grown from BZ9S09-0133W seed with plants of another wheat cultivar that comprise the desired trait or locus, selecting F1 progeny plants that comprise the desired trait or locus to produce selected F1 progeny plants, crossing the selected progeny plants with the BZ9S09-0133W plants to produce backcross progeny plants, selecting for backcross progeny plants that have the desired trait or locus and the morphological characteristics of wheat cultivar BZ9S09-0133W to produce selected backcross progeny plants, and backcrossing to BZ9S09-0133W three or more times in succession to produce selected fourth or higher backcross progeny plants that comprise said trait or locus. The modified BZ9S09-0133W may be further characterized as having essentially all of the morphological and physiological characteristics of wheat cultivar BZ9S09-0133W listed in Table 1, as determined at the 5% significance level when grown in the same environmental conditions and/or may be characterized by percent similarity or identity to BZ9S09-0133W as determined by SSR markers. The above method may be utilized with fewer backcrosses in appropriate situations, such as when the donor parent is highly related or markers are used in the selection step. Desired nucleic acids that may be used include those nucleic acids known in the art, some of which are listed herein, that will affect traits through nucleic acid expression or inhibition. Desired loci include the introgression of FRT, Lox, and other sites for site specific integration, which may also affect a desired trait if a functional nucleic acid is inserted at the integration site.

In addition, the above process and other similar processes described herein may be used to produce first generation progeny wheat seed by adding a step at the end of the process that comprises crossing BZ9S09-0133W with the introgressed trait or locus with a different wheat plant and harvesting the resultant first generation progeny wheat seed.

A further embodiment of the invention is a back-cross conversion of wheat cultivar BZ9S09-0133W. A backcross conversion occurs when DNA sequences are introduced through traditional (non-transformation) breeding techniques, such as backcrossing. DNA sequences, whether naturally occurring or transgenes, may be introduced using these traditional breeding techniques. Desired traits transferred through this process include, but are not limited to nutritional enhancements, industrial enhancements, disease resistance or tolerance, insect resistance or tolerance, herbicide tolerance or resistance, agronomic enhancements, grain quality enhancement, waxy starch, breeding enhancements, seed production enhancements, and male sterility. Descriptions of some of the cytoplasmic male sterility genes, nuclear male sterility genes, chemical hybridizing agents, male fertility restoration genes, and methods of using the aforementioned are known. Examples of genes for other traits include: Leaf rust resistance genes (Lr series such as Lr1, Lr10, Lr21, Lr22, Lr22a, Lr32, Lr37, Lr41, Lr42, and Lr43), *Fusarium* head blight-resistance genes (QFhs.ndsu-3B and QFhs.ndsu-2A), powdery mildew resistance genes (Pm21), common bunt resistance genes (Bt-10), and wheat streak mosaic virus resistance gene (Wsml), Russian wheat aphid resistance genes (Dn series such as Dn1, Dn2, Dn4, and Dn5), Black stem rust resistance genes (Sr38), Yellow rust resistance genes (Yr series such as Yr 1, YrSD, Yrsu, Yr17, Yr15, and YrH52), aluminum tolerance genes (Alt (BH)), dwarf genes (Rht), vernalization genes (Vrn), Hessian fly resistance genes (H9, H10, H21, and H29), grain color genes (R/r), glyphosate resistance genes (EPSPS), glufosinate genes (bar, pat) and water stress tolerance genes (Hva 1 and mt1D). The trait of interest is transferred from the donor parent to the recurrent parent, which in this case is the wheat plant disclosed herein, BZ9S09-0133W. Single gene traits may result from either the transfer of a dominant allele or a recessive allele. Selection of progeny containing the trait of interest is done by direct selection for a trait associated with a dominant allele. Selection of progeny for a trait that is transferred via a recessive allele requires growing and selfing the first backcross to determine which plants carry the recessive alleles. Recessive traits may require additional progeny testing in successive backcross generations to determine the presence of the gene of interest.
Using BZ9S09-0133W to Develop Other Wheat Varieties Wheat varieties such as BZ9S09-0133W are typically developed for use in seed and grain production. However, wheat varieties such as BZ9S09-0133W also provide a source of breeding material that may be used to develop new wheat varieties. Plant breeding techniques known in the art and used in a wheat plant breeding program include, but are not limited to, recurrent selection, mass selection, bulk selection, mass selection, backcrossing, pedigree breeding, open pollination breeding, restriction fragment length polymorphism enhanced selection, genetic marker enhanced selection, making double haploids, and transformation. Often, combinations of these techniques are used. The development of wheat varieties in a plant breeding program requires, in general, the development and evaluation of homozygous varieties. There are many analytical methods available to evaluate a new variety. The oldest and most traditional method of analysis is the observation of phenotypic traits but genotypic analysis may also be used.
Additional Breeding Methods In an embodiment, this invention is directed to methods for producing a wheat plant by crossing a first parent wheat plant with a second parent wheat plant wherein either the first or second parent wheat plant is cultivar BZ9S09-0133W. The other parent may be any other wheat plant, such as a wheat plant that is part of a synthetic or natural population. Any such methods using wheat cultivar BZ9S09-0133W are part of this invention: selfing, sibbing, backcrosses, mass selection, pedigree breeding, bulk selection, hybrid production, and crosses to populations. These methods are well known in the art and some of the more commonly used breeding methods are described below.

The following describes breeding methods that may be used with wheat cultivar BZ9S09-0133W in the development of further wheat plants. One such embodiment is a method for developing a cultivar BZ9S09-0133W progeny wheat plant in a wheat plant breeding program comprising: obtaining the wheat plant, or a part thereof, of cultivar BZ9S09-0133W utilizing said plant or plant part as a source of breeding material and selecting a wheat cultivar BZ9S09-0133W progeny plant with molecular markers in common with cultivar BZ9S09-0133W and/or with morphological and/or physiological characteristics selected from the characteristics listed in the Tables herein. Breeding steps that may be used in the wheat plant breeding program include pedigree breeding, backcrossing, mutation breeding, and recurrent selection. In conjunction with these steps, techniques such as RFLP-enhanced selection, genetic marker enhanced selection (e.g., SSR markers) and the making of double haploids may be utilized.

Another method involves producing a population of wheat cultivar BZ9S09-0133W progeny wheat plants, comprising crossing cultivar BZ9S09-0133W with another wheat plant, thereby producing a population of wheat plants, which, on average, derive 50% of their alleles from wheat cultivar BZ9S09-0133W. A plant of this population may be selected and repeatedly selfed or sibbed with a wheat cultivar resulting from these successive filial generations. One embodiment of this invention is the wheat cultivar produced by this method and that has obtained at least 50% of its alleles from wheat cultivar BZ9S09-0133W.

One of ordinary skill in the art of plant breeding would know how to evaluate the traits of two plant varieties to determine if there is no significant difference between the two traits expressed by those varieties. Thus the invention includes wheat cultivar BZ9S09-0133W progeny wheat plants comprising a combination of at least two cultivar BZ9S09-0133W traits selected from the group consisting of those listed in the Tables herein, so that said progeny wheat plant is not significantly different for said traits than wheat cultivar BZ9S09-0133W. Using techniques described herein, molecular markers may be used to identify said progeny plant as a wheat cultivar BZ9S09-0133W progeny plant. Mean trait values may be used to determine whether trait differences are significant, and the traits may be measured on plants grown under the same environmental conditions. Once such a variety is developed its value is substantial, as it is important to advance the germplasm base as a whole in order to maintain or improve traits such as yield, disease resistance or tolerance, pest resistance or tolerance, and plant performance in extreme environmental conditions.

Progeny of wheat cultivar BZ9S09-0133W may also be characterized through their filial relationship with wheat cultivar BZ9S09-0133W, as for example, being within a certain number of breeding crosses of wheat cultivar BZ9S09-0133W. A breeding cross is a cross made to introduce new genetics into the progeny, and is distinguished from a cross, such as a self or a sib cross, made to select among existing genetic alleles. The lower the number of breeding crosses in the pedigree, the closer the relationship between wheat cultivar BZ9S09-0133W and its progeny. For example, progeny produced by the methods described herein may be within 1, 2, 3, 4 or 5 breeding crosses of wheat cultivar BZ9S09-0133W.
Pedigree Breeding Pedigree breeding starts with the crossing of two genotypes, such as BZ9S09-0133W and another wheat variety having one or more desirable characteristics that is lacking or which complements BZ9S09-0133W. If the two original parents do not provide all the desired characteristics, other sources can be included in the breeding population. In the pedigree method, superior plants are selfed and selected in successive filial generations. In the succeeding filial generations the heterozygous condition gives way to homogeneous varieties as a result of self-pollination and selection. Typically in the pedigree method of breeding, five or more successive filial generations of selfing and selection is practiced: F1 to F2; F2 to F3; F3 to F4; F4 to F5, etc. After a sufficient amount of inbreeding, successive filial generations will serve to increase seed of the developed variety. In an embodiment, the developed variety comprises homozygous alleles at about 95% or more of its loci.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, a wheat variety may be crossed with another variety to produce a first generation progeny plant. The first generation progeny plant may then be backcrossed to one of its parent varieties to create a BC1 or BC2. Progeny are selfed and selected so that the newly developed variety has many of the attributes of the recurrent parent and yet several of the desired attributes of the non-recurrent parent. This approach leverages the value and strengths of the recurrent parent for use in new wheat varieties.

Therefore, an embodiment of this invention is a method of making a backcross conversion of wheat cultivar BZ9S09-0133W comprising the steps of crossing a plant of wheat cultivar BZ9S09-0133W with a donor plant comprising a desired trait, selecting an F1 progeny plant comprising the desired trait, and backcrossing the selected F1 progeny plant to a plant of wheat cultivar BZ9S09-0133W. This method may further comprise the step of obtaining a molecular marker profile of wheat cultivar BZ9S09-0133W and using the molecular marker profile to select for a progeny plant with the desired trait and the molecular marker profile of BZ9S09-0133W. In one embodiment, the desired trait is a mutant gene or transgene present in the donor parent.

Recurrent Selection and Mass Selection

Recurrent selection is a method used in a plant breeding program to improve a population of plants. BZ9S09-0133W is suitable for use in a recurrent selection program. The method entails individual plants cross pollinating with each other to form progeny. The progeny are grown and the superior progeny selected by any number of selection methods, which include individual plant, half-sib progeny, full-sib progeny and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic cultivar. A synthetic cultivar is the resultant progeny formed by the intercrossing of several selected varieties.

Mass selection is a useful technique when used in conjunction with molecular marker enhanced selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Also, instead of self pollination, directed pollination could be used as part of the breeding program.

Mutation Breeding

Mutation breeding is another method of introducing new traits into wheat cultivar BZ9S09-0133W. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation, such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (optionally from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. In addition, mutations created in other wheat plants may be used to produce a backcross conversion of wheat cultivar BZ9S09-0133W that comprises such mutation. Further embodiments of the invention are the treatment of BZ9S09-0133W with a mutagen and the plant produced by mutagenesis of BZ9S09-0133W.

Breeding with Molecular Markers

Molecular markers, which include markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) and Single Nucleotide Polymorphisms (SNPs), may be used in plant breeding methods utilizing wheat cultivar BZ9S09-0133W. Isozyme Electrophoresis and RFLPs have been widely used to determine genetic composition.

SSR technology is currently the most efficient and practical marker technology; more marker loci can be routinely used and more alleles per marker locus can be found using SSRs in comparison to RFLPs. Single Nucleotide Polymorphisms (SNPs) may also be used to identify the unique genetic composition of the invention and progeny varieties retaining that unique genetic composition. Various molecular marker techniques may be used in combination to enhance overall resolution. Wheat DNA molecular marker linkage maps have been rapidly constructed and widely implemented in genetic studies.

One use of molecular markers is QTL mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Production of Double Haploids

The production of double haploids can also be used for the development of plants with a homozygous phenotype in the breeding program. For example, a wheat plant for which wheat cultivar BZ9S09-0133W is a parent can be used to produce double haploid plants. Double haploids are produced by the doubling of a set of chromosomes (1N) from a heterozygous plant to produce a completely homozygous individual. This can be advantageous because the process omits the generations of selfing needed to obtain a homozygous plant from a heterozygous source.

Haploid induction systems have been developed for various plants to produce haploid tissues, plants and seeds. The haploid induction system can produce haploid plants from any genotype by crossing a selected line (as female) with an inducer line. Such inducer lines for maize include Stock 6. Methods for obtaining haploid plants have also been disclosed in the art.

Thus, an embodiment of this invention is a process for making a substantially homozygous BZ9S09-0133W progeny plant by producing or obtaining a seed from the cross of BZ9S09-0133W and another wheat plant and applying double haploid methods to the F1 seed or F1 plant, or to any successive filial generation. Based on studies in maize and currently being conducted in wheat, such methods would decrease the number of generations required to produce a variety with similar genetics or characteristics to BZ9S09-0133W.

In particular, a process of making seed retaining the molecular marker profile of wheat cultivar BZ9S09-0133W is contemplated, such process comprising obtaining or producing F1 seed for which wheat cultivar BZ9S09-0133W is a parent, inducing doubled haploids to create progeny without the occurrence of meiotic segregation, obtaining the molecular marker profile of wheat cultivar BZ9S09-0133W, and selecting progeny that retain the molecular marker profile of BZ9S09-0133W. Descriptions of other breeding methods that are commonly used for different traits and crops are known.

Further reproduction of the variety can occur by tissue culture and regeneration. Tissue culture of various tissues of wheat and regeneration of plants therefrom is well known and widely published. Thus, another aspect of this invention is to provide cells which upon growth and differentiation produce wheat plants having essentially all of the morphological and physiological characteristics of wheat cultivar BZ9S09-0133W. Means for preparing and maintaining plant tissue culture are well known in the art. By way of example, a tissue culture comprising organs has been used to produce regenerated plants.

Tables

In Table 2, yield and agronomic characteristics collected in 2012 in Washington, Montana, and Idaho for wheat cultivar BZ9S09-0133W are compared to two commercial check cultivars. Column 1 shows the cultivar, column 2 shows the yield as a percent of the trial average, column 3 shows the test weight of harvested grain in pounds per bushel, column 4 shows the plant height in centimeters, column 5 shows the Julian flowering date when 50% of the variety flowers, column 6 shows the grain protein % on a 12% moisture basis, column 7 shows the SDS Sedimentation in mm, and column 8 shows Stripe Rust resistance with 1 being very resistant and 9 being very susceptible.

In Table 3, yield and agronomic characteristics collected in 2013 in Washington, Montana, and Idaho for wheat cultivar BZ9S09-0133W are compared to two commercial check cultivars. Column 1 shows the cultivar, column 2 shows the yield as a percent of the trial average, column 3 shows the test weight of harvested grain in pounds per bushel, column 4 shows the plant height in centimeters, column 5 shows the Julian flowering date when 50% of the variety flowers.

TABLE 2

2012 Comparative Data for Cultivar BZ9S09-0133W and Selected Varieties

| | 2 | 3 | 4 | 5 | 6 | 7 | 8 |
|---|---|---|---|---|---|---|---|
| | | | | Characteristic | | | |
| | Yield | Test Weight | Plant Height | Flowering Date | % Protein | SDS | Stripe Rust |
| | | | | Unit of measure | | | |
| 1 | % of average | lbs/bu | cm | Julian | 12% mb | mm | 1 to 9* |
| Variety | | | | | | | |
| WB-HARTLINE | 104.9 | 59.0 | 91.4 | 186 | 14.0 | 104.7 | 3 |
| WB-IDAMAX | 106.3 | 60.1 | 83.8 | 185 | 13.8 | 110.3 | 4 |
| Average | 100.0 | 61.1 | 79.8 | 185.5 | 13.9 | 110.3 | 2.7 |
| BZ9S09-0133W | 97.9 | 61.4 | 73.7 | 183 | 14.4 | 112.8 | 1 |
| No. of replications | 21 | 12 | 21 | 3 | 21 | 21 | 3 |

*1 being very resistant and 9 being very susceptible

TABLE 3

2013 Comparative Data for Cultivar BZ9S09-0133W and Selected Varieties

| | 2 | 3 | 4 | 5 |
|---|---|---|---|---|
| | | | Characteristic | |
| | Yield | Test Weight | Plant Height | Flowering Date |
| | | | Unit of measure | |
| 1 | % of average | lbs/bu | cm | Julian |
| Variety | | | | |
| WB-HARTLINE | 95.0 | 57.0 | 86.4 | 181 |
| WB-IDAMAX | 107.2 | 60.1 | 81.3 | 180 |
| Average | 100.0 | 60.1 | 78.0 | 178.8 |
| BZ9S09-0133W | 96.8 | 60.5 | 73.7 | 177 |
| No. of replications | 24 | 24 | 24 | 4 |

Definitions

In the description and tables, a number of terms are used. In order to provide a clear and consistent understanding of the specification and claims, the following definitions are provided:

A: When used in conjunction with the word "comprising" or other open language in the claims, the words "a" and "an" denote "one or more."

About: Refers to embodiments or values that include the standard deviation of the mean for a given item being measured.

Allele: Any of one or more alternative forms of a gene locus, all of which relate to one trait or characteristic. In a diploid cell or organism, the two alleles of a given gene occupy corresponding loci on a pair of homologous chromosomes.

Aphids: Aphid resistance is scored on a scale from 1 to 9; a score of 4 or less indicates resistance. Varieties scored as 1 to 5 appear normal and healthy, with numbers of aphids increasing from none to up to 300 per plant. A score of 7 indicates that there are 301 to 800 aphids per plant and that the plants show slight signs of infestation. A score of 9 indicates severe infestation and stunted plants with severely curled and yellow leaves.

Awn: Awn is intended to mean the elongated needle-like appendages on the flower- and seed-bearing head at the top of the cereal grain plant (e.g., wheat, common wheat, rye). Awns are attached to the lemmas. Lemmas enclose the stamen and the stigma as part of the florets. Florets are grouped in spikelets, which in turn together comprise the head.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Cell: As used herein, the term cell includes a plant cell, whether isolated, in tissue culture, or incorporated in a plant or plant part.

Chromatography: A technique wherein a mixture of dissolved substances are bound to a solid support followed by passing a column of fluid across the solid support and varying the composition of the fluid. The components of the mixture are separated by selective elution.

Crossing: The mating of two parent plants.

Cross-pollination: Fertilization by the union of two gametes from different plants.

Disease Resistance: As used herein, the term disease resistance or disease resistant is defined as the ability of plants to restrict the activities of a specified disease, such as a fungus, virus, or bacterium.

Disease Tolerance: As used herein, the term disease tolerance or disease tolerant is defined as the ability of plants to endure a specified disease (such as a fungus, virus, or bacterium) or an adverse environmental condition and still perform and produce in spite of this disorder.

Emasculate: The removal of plant male sex organs or the inactivation of the organs with a cytoplasmic or nuclear genetic factor or a chemical agent conferring male sterility.

Embryo: The embryo is the small plant contained within a mature seed.

Emergence (EMR): The emergence score describes the ability of a seed to emerge from the soil after planting. Each genotype is given a 1 to 9 score based on its percent of emergence. A score of 1 indicates an excellent rate and percent of emergence, an intermediate score of 5 indicates an average rating and a 9 score indicates a very poor rate and percent of emergence.

Enzymes: Molecules which can act as catalysts in biological reactions.

Essentially all of the morphological and physiological characteristics: The characteristics of a plant are recovered that are otherwise present when compared in the same environment, other than occasional variant traits that might arise during backcrossing or direct introduction of a transgene.

$F_1$ Hybrid: The first generation progeny of the cross of two nonisogenic plants.

Gene Converted (Conversion): Gene conversion or a gene converted plant refers to plants that are developed by backcrossing, genetic engineering, or mutation, wherein essentially all of the morphological and physiological characteristics of a variety are recovered, in addition to the one or more traits transferred into the variety via the backcrossing technique, genetic engineering, or mutation.

Gene Silencing: Gene silencing refers to the interruption or suppression of the expression of a gene at the level of transcription or translation.

Genotype: The genetic constitution of a cell or organism.

Glume Blotch: Glume Blotch is a disease of wheat characterized by small, irregular gray to brown spots or blotches on the glumes, although infections may also occur at the nodes. The disease is caused by the fungus *Stagonosporum nodorum* (may also be referred to as *Septoria nodorum*). Resistance to this disease is scored on scales that reflect the observed extent of the disease on the leaves of the plant. Rating scales may differ but in general a low number indicates resistance and higher number suggests different levels of susceptibility.

Haploid: A cell or organism having one set of the two sets of chromosomes in a diploid.

Head: As used herein, the term head refers to a group of spikelets at the top of one plant stem. The term spike also refers to the head of a plant located at the top of one plant stem.

Herbicide Resistance: As used herein, the term herbicide resistance or herbicide resistant is defined as the ability of plants to survive and reproduce following exposure to a dose of herbicide that would normally be lethal to the plant.

Herbicide Tolerance: As used herein, the term herbicide tolerance or herbicide tolerant is defined as the ability of plants to survive and reproduce after herbicide treatment.

Insect Resistance: As used herein, the term disease resistance or disease resistant is defined as the ability of plants to restrict the activities of a specified insect or pest.

Insect Tolerance: As used herein, the term disease tolerance or disease tolerant is defined as the ability of plants to endure a specified insect or pest and still perform and produce in spite of this disorder.

Kernel Weight: As used herein, the term kernel weight refers to the weight of individual kernels (also called seeds), often reported as the weight of one thousand kernels or "1000 Kernel Weight."

Leaf Rust: Leaf Rust is a disease of wheat characterized by pustules that are circular or slightly elliptical, that usually do not coalesce, and contain masses of orange to orange-brown spores. The disease is caused by the fungus *Puccinia recondita* f. sp. *tritici*. Infection sites primarily are found on the upper surfaces of leaves and leaf sheaths, and occasionally on the neck and awns. Resistance to this disease is scored on scales that reflect the observed extent of the disease on the leaves of the plant. Rating scales may differ but in general a low number indicates resistance and higher number suggests different levels of susceptibility.

Linkage: A phenomenon wherein alleles on the same chromosome tend to segregate together more often than expected by chance if their transmission was independent.

Locus: A locus is a position on a genomic sequence that is usually found by a point of reference, for example, the position of a DNA sequence that is a gene, or part of a gene or intergenic region. A locus confers one or more traits such as, for example, male sterility, herbicide tolerance or resistance, insect resistance or tolerance, disease resistance or tolerance, modified fatty acid metabolism, modified phytic acid metabolism, modified carbohydrate metabolism or modified protein metabolism. The trait may be, for example, conferred by a naturally occurring gene introduced into the genome of the variety by backcrossing, a natural or induced mutation, or a transgene introduced through genetic transformation techniques. A locus may comprise one or more alleles integrated at a single chromosomal location.

Marker: A readily detectable phenotype, preferably inherited in codominant fashion (both alleles at a locus in a diploid heterozygote are readily detectable), with no environmental variance component, i.e., heritability of 1.

Maturity: As used herein, the term maturity refers to the stage of plant growth at which the development of the kernels is complete.

Or: As used herein is meant to mean "and/or" and be interchangeable therewith unless explicitly indicated to refer to the alternative only.

Pedigree Distance: Pedigree distance is the relationship among generations based on their ancestral links as evidenced in pedigrees. It may be measured by the distance of the pedigree from a given starting point in the ancestry.

Percent Identity: Percent identity, as used herein, refers to the comparison of the homozygous alleles of two wheat varieties. Percent identity is determined by comparing a statistically significant number of the homozygous alleles of two developed varieties. For example, a percent identity of 90% between wheat variety 1 and wheat variety 2 means that the two varieties have the same allele at 90% of their loci.

Percent Similarity: Percent similarity as used herein refers to the comparison of the homozygous alleles of a wheat variety such as BZ9S09-0133W with another plant, and if the homozygous allele of BZ9S09-0133W matches at least one of the alleles from the other plant then they are scored as similar. Percent similarity is determined by comparing a statistically significant number of loci and recording the number of loci with similar alleles as a percentage. A percent similarity of 90% between BZ9S09-0133W and another plant means that BZ9S09-0133W matches at least one of the alleles of the other plant at 90% of the loci.

Phenotype: The detectable characteristics of a cell or organism, which characteristics are the manifestation of gene expression.

Plant: As used herein, the term plant includes reference to an immature or mature whole plant, including a plant from which seed, grain, or anthers have been removed. A seed or embryo that will produce the plant is also considered to be a plant.

Plant Height (Hgt): As used herein, the term plant height is defined as the average height in inches or centimeters of a group of plants, as measured from the ground level to the tip of the head, excluding awns.

Plant Parts: As used herein, the term plant parts (or reference to "a wheat plant, or a part thereof") includes, but is not limited to, protoplasts, callus, leaves, stems, roots, root tips, anthers, pistils, seed, grain, pericarp, embryo, pollen, ovules, cotyledon, hypocotyl, spike, floret, awn, lemma, shoot, tissue, petiole, cells, and meristematic cells.

Powdery Mildew: Powdery Mildew is a disease of wheat characterized by white to pale gray, fuzzy or powdery colonies of mycelia, and conidia on the upper surfaces of leaves and leaf sheaths (especially on lower leaves), and sometimes on the spikes. The disease is caused by the fungus *Erysiphe graminis* f. sp. *tritici*. Older fungal tissue is yellowish gray. This superficial fungal material can be rubbed off easily with the fingers. Host tissue beneath the fungal material becomes chlorotic or necrotic and, with severe infections, the leaves may die. Eventually, black spherical fruiting structures may develop in the mycelia, and can be seen without magnification. Resistance to this disease is scored on scales that reflect the observed extent of the disease on the leaves of the plant. Rating scales may differ but in general a low number indicates resistance and higher number suggests different levels of susceptibility.

Progeny: As used herein, progeny includes an F1 wheat plant produced from the cross of two wheat plants where at least one plant includes wheat cultivar BZ9S09-0133W. Progeny further includes, but is not limited to, subsequent $F_2$, $F_3$, $F_4$, $F_5$, $F_6$, $F_7$, $F_8$, $F_9$ and $F_{10}$ generational crosses with the recurrent parental line.

Quantitative Trait Loci (QTL): Quantitative trait loci refer to genetic loci that control to some degree numerically representable traits that are usually continuously distributed.

Regeneration: The development of a plant from tissue culture.

*Rhizoctonia* Root Rot: *Rhizoctonia* Root Rot is a disease of wheat characterized by sharp eyespot lesions that develop on basal leaf sheaths. The disease is caused by the fungus *Rhizoctonia solani*. The lesion margins are dark brown with pale, straw-colored centers and the mycelia often present in the centers of lesions are easily removed by rubbing. Roots can also be affected, usually becoming brown in color and reduced in number. The disease can cause stunting and a reduction in the number of tillers. Resistance to this disease is scored on scales that reflect the observed extent of the disease on the leaf sheaths of the plant and on reduced vigor of the plant. Rating scales may differ but in general a low number indicates resistance and higher number suggests different levels of susceptibility.

Scab or Head Blight: Scab or Head Blight a disease of wheat characterized by florets (especially the outer glumes) that become slightly darkened and oily in appearance. The disease is caused by the fungus *Fusarium* which has numerous species. Spores are produced that can give the spike and shriveled, infected kernels a bright pinkish color. Spores can produce a toxin, deoxynivalenol which can be measured with a chemical test. Resistance to this disease can be measured in three ways: the extent of the disease on the spikes of the plant, the percent kernels which are visibly shriveled and the amount of deoxynivalenol in the kernels. Rating scales may differ but in general a low number indicates resistance and higher number suggests different levels of susceptibility.

SDS Sedimentation: SDS sedimentation (sodium dodecyl sedimentation) test values are a measure of the end-use mixing and handling properties of bread dough and their relation to bread-making quality as a result of the dough's gluten quality. Higher SDS sedimentation levels reflect higher gluten quality.

Self-pollination: The transfer of pollen from the anther to the stigma of the same plant.

*Septoria* Leaf Blotch or Speckled Leaf Blotch: Speckled leaf blotch is a disease of wheat, common wheat and durum wheat characterized by irregularly shaped blotches that are at first yellow and then turn reddish brown with grayish brown dry centers, caused by the rust fungus *Septoria tritici*. Resistance to this disease is scored on scales that reflect the observed extent of the disease on the leaves of the plant. Rating scales may differ but in general a low number indicates resistance and higher number suggests different levels of susceptibility.

Single Locus Converted (Conversion) Plant: Plants which are developed by a plant breeding technique called backcrossing and/or by genetic transformation to introduce a given locus that is transgenic in origin, wherein essentially all of the morphological and physiological characteristics of a wheat cultivar are recovered in addition to the characteristics of the locus transferred into the variety via the backcrossing technique or by genetic transformation. It is understood that once introduced into any wheat plant genome, a locus that is transgenic in origin (transgene), can be introduced by backcrossing as with any other locus.

Soil Born Mosaic Virus: Soil born mosaic virus is a disease of wheat characterized by mild green to yellow mosaic, yellow-green mottling, dashes, and parallel streaks, most clearly visible on the youngest leaf. Reddish streaking and necrosis at leaf tips sometimes occurs. Stunting can be moderate to severe, depending on the variety. The disease is caused by a virus which is transmitted by a soilborne fungus-like organism, *Polymyxa graminis*, which makes swimming spores that infect the roots of wheat. Resistance to this disease is scored on scales that reflect the observed extent of the disease on the young plants. Rating scales may differ, but in general, a low number indicates resistance and a higher number suggests different levels of susceptibility.

Substantially Equivalent: A characteristic that, when compared, does not show a statistically significant difference (e.g., p=0.05) from the mean.

Stem Rust: Stem Rust is a disease of wheat characterized by pustules containing masses of spores that are dark reddish brown, and may occur on both sides of the leaves, on the stems, and on the spikes. The disease is caused by the fungus *Puccinia graminis* f. sp. *Tritici*. Resistance to this disease is scored on scales that reflect the observed extent of the disease on the leaves of the plant. Rating scales may differ, but in general, a low number indicates resistance and a higher number suggests different levels of susceptibility.

Stripe Rust: Stripe rust is a disease of wheat, common wheat, durum wheat, and barley characterized by elongated rows of yellow spores on the affected parts, caused by a rust fungus, *Puccinia striiformis*. Resistance to this disease is scored on scales that reflect the observed extent of the disease on the leaves of the plant. Rating scales may differ, but in general, a low number indicates resistance and a higher number suggests different levels of susceptibility.

Test Weight (TWT): As used herein, the term test weight is a measure of density that refers to the weight in pounds of the amount of kernels contained in a bushel unit of volume.

Tissue Culture: A composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, ovules, pericarp, flowers, florets, heads, spikelets, seeds, leaves, stems, roots, root tips, anthers, pistils, awns, stems, and the like.

Transgene: A genetic locus comprising a sequence which has been introduced into the genome of a wheat plant by transformation.

DEPOSIT INFORMATION

A deposit of the wheat cultivar BZ9S09-0133W, which is disclosed herein above and referenced in the claims, was made with the American Type Culture Collection (ATCC), 10801 University Blvd., Manassas, Va 20110-2209. The date of deposit is Aug. 04, 2016 and the accession number for those deposited seeds of wheat cultivar BZ9S09-0133W is ATCC Accession No. PTA-123418. All restrictions upon the deposit have been removed, and the deposit is intended to meet all of the requirements of 37 C.F.R. §1.801-1.809. The deposit will be maintained in the depository for a period of 30 years, or 5 years after the last request, or for the effective life of the patent, whichever is longer, and will be replaced if necessary during that period.

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

The references cited herein, to the extent that they provide exemplary procedural or other details supplementary to those set forth herein, are specifically incorporated herein by reference.

What is claimed is:

1. A plant of wheat cultivar BZ9S09-0133W, wherein a sample of seed of said cultivar has been deposited under ATCC Accession No. PTA-123418.

2. A plant part of the plant of claim 1, wherein the plant part comprises at least one cell of said plant.

3. The plant part of claim 2, further defined as head, awn, leaf, pollen, ovule, embryo, cotyledon, hypocotyl, meristematic cell, root, root tip, pistil, anther, floret, seed, pericarp, spike, stem, and callus.

4. A tissue culture produced from the plant part of claim 3.

5. A wheat plant regenerated from the tissue culture of claim 4.

6. A seed of wheat cultivar BZ9S09-0133W, wherein a sample of seed of said cultivar has been deposited under ATCC Accession No. PTA-123418.

7. A method of producing wheat seed, wherein the method comprises crossing the plant of claim 1 with itself or a second wheat plant.

8. The method of claim 7, wherein the method is further defined as comprising crossing the plant of wheat cultivar BZ9S09-0133W with a second, distinct wheat plant to produce an $F_1$ hybrid wheat seed.

9. An $F_1$ hybrid wheat seed produced by the method of claim 8.

10. An $F_1$ hybrid wheat plant produced by growing the seed of claim 9.

11. A composition comprising the seed of claim 6 comprised in plant seed growth media, wherein a sample of seed of said cultivar has been deposited under ATCC Accession No. PTA-123418.

12. The composition of claim 11, wherein the growth media is soil or a synthetic cultivation medium.

13. A plant of wheat cultivar BZ9S09-0133W, further comprising a single locus conversion, wherein a sample of seed of wheat cultivar BZ9S09-0133W has been deposited under ATCC Accession No. PTA-123418.

14. The plant of claim 13, wherein the single locus conversion comprises a transgene.

15. A seed that produces the plant of claim 13.

16. The seed of claim 15, wherein the single locus confers a trait selected from the group consisting of male sterility, herbicide tolerance, insect resistance, pest resistance, disease resistance, modified fatty acid metabolism, abiotic stress resistance, altered seed amino acid composition, site-specific genetic recombination, and modified carbohydrate metabolism.

17. The seed of claim 16, wherein the single locus confers tolerance to an herbicide selected from the group consisting of glyphosate, sulfonylurea, imidazolinone, dicamba, glufosinate, phenoxy propionic acid, L-phosphinothricin, cyclohexanone, cyclohexanedione, triazine, and benzonitrile.

18. The seed of claim 16, wherein the single locus further comprises a gene encoding a *Bacillus thuringiensis* (Bt) endotoxin.

19. The seed of claim 16, wherein the single locus further comprises a gene encoding a protein selected from the group consisting of glutenins, gliadins, phytase, fructosyltransferase, levansucrase, α-amylase, invertase and starch branching enzyme or encoding an antisense of stearyl-ACP desaturase.

20. The seed of claim 15, wherein the single locus conversion comprises a transgene.

21. The method of claim 8, wherein the method further comprises:

(a) crossing a plant grown from said $F_1$ hybrid wheat seed with itself or a different wheat plant to produce a seed of a progeny plant of a subsequent generation;

(b) growing a progeny plant of a subsequent generation from said seed of a progeny plant of a subsequent generation and crossing the progeny plant of a subsequent generation with itself or a second plant to produce a progeny plant of a further subsequent generation; and (c) repeating steps (a) and (b) using said progeny plant of a further subsequent generation from step (b) in place of the plant grown from said $F_1$ hybrid wheat seed in step (a), wherein steps (a) and (b) are repeated with sufficient inbreeding to produce an inbred wheat plant derived from the wheat cultivar BZ9S09-0133W.

22. A method of producing a commodity plant product comprising collecting the commodity plant product from the plant of claim 1.

23. The method of claim 22, wherein the commodity plant product is grain, flour, baked goods, cereals, pasta, beverages, livestock feed, biofuel, straw, construction materials, and starches.

24. A wheat commodity plant product produced by the method of claim 23, wherein the commodity plant product comprises at least one cell of wheat cultivar BZ9S09-0133W.

* * * * *